(12) United States Patent
Didier (10) Patent No.: US 12,383,180 B2
(45) Date of Patent: Aug. 12, 2025

(54) EMBEDDED DEVICE FOR SYNCHRONIZED COLLECTION OF BRAINWAVES AND ENVIRONMENTAL DATA

(71) Applicant: MENTALISTA, Villejuif (FR)

(72) Inventor: Bastien Didier, Villejuif (FR)

(73) Assignee: MENTALISTA, Villejuif (FR)

( * ) Notice: Subject to any disclaimer, the term of this patent is extended or adjusted under 35 U.S.C. 154(b) by 434 days.

(21) Appl. No.: 18/046,759

(22) Filed: Oct. 14, 2022

(65) Prior Publication Data

US 2023/0121215 A1 Apr. 20, 2023

(30) Foreign Application Priority Data

Oct. 15, 2021 (EP) .................... 21306444

(51) Int. Cl.
*A61B 5/16* (2006.01)
*A61B 5/00* (2006.01)

(52) U.S. Cl.
CPC ............ *A61B 5/165* (2013.01); *A61B 5/6803* (2013.01)

(58) Field of Classification Search
None
See application file for complete search history.

(56) References Cited

U.S. PATENT DOCUMENTS

| | | |
|---|---|---|
| 2019/0294243 A1 | 9/2019 | Laszlo |
| 2019/0387998 A1 | 12/2019 | Garten |
| 2020/0142481 A1* | 5/2020 | Lee .................. G06F 3/015 |

FOREIGN PATENT DOCUMENTS

| | | |
|---|---|---|
| WO | WO 2014/116826 | 7/2014 |
| WO | WO 2018/156992 | 8/2018 |

OTHER PUBLICATIONS

ThoughtViz Visualizing Human Thoughts Using Generative Adversarial Network Ultimedia, ACM, 2 Penn Plaza, Suite 701 New York NY 10121-0701 USA, Oct. 15, 2018 (Oct. 15, 2018), pp. 950-958, XP058544185, DOI: 10.1145/3240508.3240641 ISBN: 978-1-4503-5665-7.
EP Search Report and Written Opinion corresponding to EP 21306444.7 dated Apr. 11, 2022.

* cited by examiner

*Primary Examiner* — Ankit D Tejani
(74) *Attorney, Agent, or Firm* — Conley Rose, P.C.

(57) ABSTRACT

A system having one or more devices for automatic brainwave analysis, configured to be worn by a user, and a remote processing unit configured to store all of the signals from said one or more devices, having
- at least one brainwave sensor, providing a stream of brain data associated with said user;
- at least one environmental sensor, providing an environmental data stream;
- means for selecting a signal extracted from said stream of brain data, for associating them with at least one corresponding signal extracted from said stream of environmental data, for storing said signals and for transmitting them to the remote processing unit, the latter comprising means for extracting classification information from said data, and for constituting a set associating said data with the extracted classification information.

8 Claims, 2 Drawing Sheets

EMBEDDED DEVICE FOR SYNCHRONIZED COLLECTION OF BRAINWAVES AND ENVIRONMENTAL DATA

CROSS-REFERENCE TO RELATED APPLICATIONS

The present application claims priority to European Application No. 21306444.7 filed with the European Patent Office on Oct. 15, 2021 and entitled "EMBEDDED DEVICE FOR SYNCHRONIZED COLLECTION OF BRAINWAVES AND ENVIRONMENTAL DATA," which is incorporated herein by reference in its entirety for all purposes.

FIELD OF THE INVENTION

The present invention relates to the field of brainwave collection via brain-machine interfaces. In particular, it aims to collect brainwaves via sensors, and to associate them with data from environmental sensors.

BACKGROUND OF THE INVENTION

Neural interfaces, or brain-machine interfaces, are a relatively new field of research, but some devices are already on the market.

The following Wikipedia page mentions a state of the art on the matter and some promising practical applications: https://fr.wikipedia.org/wiki/Interface_neuronale_directe One may cite, for example helping physically disabled people to act on their environment using only their thoughts.

The company Emotiv Systems markets an EPOC+ helmet equipped with 14 electroencephalographic (EEG) electrodes distributed over the user's skull.

Such a device therefore makes it possible to acquire brain data streams, relating to the user's mental activity. It is then possible to process this data in order to trigger an action such as controlling of an object, for example.

However, this processing is extremely difficult because there is no way to associate a signal extracted from this brain data with such a semantic value that could then trigger an appropriate action.

The article "*ThroughtViz: Visualizing Human Thoughts Using Generative Adversarial Network*" by Praveen Tirurpattur, Concetto Spampinato, Yogesh Singh Rawat, and Mubarak Shah, in 2018 ACM Multimedia Conference on Multimedia Conference, MINI 2018, Seoul, Republic of Korea, Oct. 22-26, 2018. pages 950-958, ACM, 2018, represents an attempt to classify brain signals using images perceived by a user.

More specifically, the paper considers the use of an artificial neural network to enable a generalization and the development of a predictive model for determining an image from brain data from an electroencephalogram (EEG).

In order to build this predictive model, the article proposes a learning phase wherein a subject sits in front of a screen and looks at a series of images in a defined sequence. When each image appears, the brain activity is sampled and labeled with the name of the image class. Once collected, the brain data is used to train generative adversarial networks (GANs for short). The objective is to make the model constituted by this network learn simplified representations of concepts like "tiger" or "the number 1", etc.

However, this approach suffers from several drawbacks. In particular, this learning process is very constraining and does not allow for a sufficiently relevant training set to allow for the construction of an efficient, accurate predictor.

SUMMARY

One objective of embodiments of the present invention is to provide a device and method that at least partially alleviates the above-mentioned shortcomings.

More particularly, according to embodiments, it is intended to enable the construction of an effective training set in an easy, inexpensive manner compared to the solutions of the state of the art.

For these purposes, embodiments of the invention is based on a device adapted to be worn by a user and having both at least one brainwave sensor and at least one environmental sensor.

The contribution of this environmental sensor and the combination of these two kinds of sensors allow new functionalities in particular and, according to one embodiment, to substantially improve a learning mechanism of a neural network.

In particular, according to a first aspect, an embodiments of the present invention can be implemented by a system comprising one or more automatic brainwave analysis devices, configured to be worn by a user, and a remote processing unit configured to store all of the signals from the one or more devices, the one or more devices comprising at least one brainwave sensor, providing a stream of brain data associated with the user;
at least one environmental sensor, providing an environmental data stream;
means for selecting a signal extracted from the brain data stream, for associating them with at least one corresponding signal extracted from the environmental data stream, for storing the signals and for transmitting them to the remote processing unit,
the remote processing unit including means for extracting classification information from the data, and for forming a set associating the data with the extracted classification information.

According to preferred embodiments, embodiments of the invention comprises one or more of the following features which may be used separately or in partial combination with each other or in total combination with each other:
at least one environmental sensor comprises a video camera, oriented so as to capture an area of space substantially corresponding to that captured by the gaze of the user;
at least one environmental sensor comprises a sound sensor;
the device further comprises a headband for holding the device in place on the user's head and for holding the brainwave sensors in contact with or in close proximity to the head; and a power supply for operating the sensors and the means;
the device is configured to associate with the signals a timestamp and/or an identifier of the device;
the location of a brain sensor depends on a type of the at least one environmental sensor;
the device further comprises means for acquiring an external data stream from a source external to the device, and for associating the signal extracted from the brain data stream with at least one corresponding signal extracted from the external data stream.
the system comprises means for training a neural network based on the set.

According to another aspect, embodiments of the invention may also be implemented by a method of automatically analyzing brainwaves using a device configured to be worn by a user, the method comprising steps of:

generating a brain data stream associated with the user by means of at least one brainwave sensor;

generating an environmental data stream by means of at least one environmental sensor;

associating a selected signal extracted from the brain data stream with at least one corresponding signal extracted from the environmental data stream;

storing the signals and transmitting to a remote processing unit extracting, by the remote processing unit, of classification information from the data, and constituting (S7) a set associating the data with the extracted classification information.

According to preferred embodiments, the invention comprises one or more of the following features which may be used separately or in partial combination with each other or in total combination with each other:

the method further comprises a step of training a neural network based on the set.

the method further comprises a step of predicting an item of classification information from at least one new signal extracted from the brain data.

According to another aspect, embodiments of the invention may also be implemented by a computer program comprising instructions for implementing the method as previously described when executed on one or more information processing platforms.

Further features and advantages of the invention will become apparent from the following description of a preferred embodiment of the invention, given by way of example and with reference to the attached drawings

BRIEF DESCRIPTION OF THE FIGURES

The attached drawings show embodiments of the invention.

DETAILED DESCRIPTION

One aspect of the invention relates to an automatic brainwave analysis device configured to be worn by a user.

Different embodiments of such a device. For example, this device can be a helmet or a headband that the user must wear.

According to one embodiment, the device has a headband provided to hold the device in place on the user's head and to hold the brainwave sensors in contact with or in close proximity to the head; and a power supply for operating the sensors and processing means.

This device further comprises at least one brainwave sensor, providing a stream of brainwave data associated with the wearing user, at least one environmental sensor, providing a stream of environmental data, and means for processing these data streams.

Figure 1:
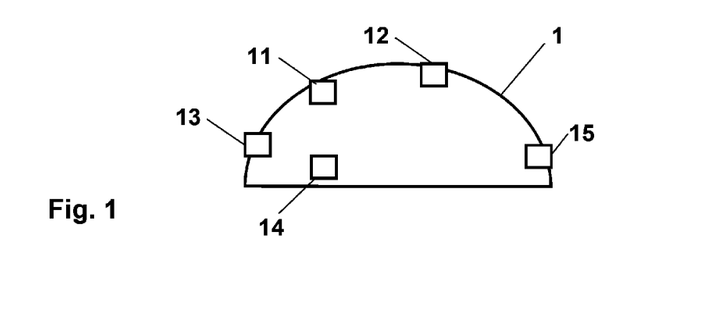
FIG. 1 is a diagram of a device according to one embodiment of the invention.

FIG. 1 is a diagram of such a device according to one embodiment of the invention.

The device 1 comprises brainwave sensors 11, 12 which can be of different types, depending on the available technologies. The different techniques for acquiring brainwaves comprise electroencephalography (EEG), functional near-infrared spectroscopy (fNIRS), and magnetoencephalography (MEG), but other techniques could be used to retrieve neuronal activity.

Furthermore, two sensors are shown for the sake of clarity in the figure, but many sensors can be positioned at different locations on the device 1 corresponding to various areas of the brain. A large number of sensors can capture brain activity in a more general way, since a sensor can only effectively acquire the activity of a limited area around its location and different parts of the brain have specialized activities (auditory cortex, visual cortex, etc.)

According to one embodiment of the invention, the location of the sensors may depend on the type of environmental sensors used.

Thus, if one of the environmental sensors is a video sensor, at least one brain sensor (or electrode) may be positioned at the visual cortex. The visual cortex covers the occipital lobe on the lateral and medial sides and overlaps with the parietal and temporal lobes. It is responsible for processing visual information. The study of the visual cortex in neuroscience has made it possible to divide it into a multitude of functional sub-regions (V1, V2, V3, V4, MT, etc.) which each or collectively process multiple properties of the information coming from the visual pathways (shapes, colors, movements, etc.). It may also be interesting to position several sensors in order to collect brain data related to these different brain activities.

If one of the environmental sensors is a sound sensor, that is a microphone, at least one brain sensor may be positioned at the auditory cortex. The auditory cortex is the part of the brain that analyzes auditory information, that is the information extracted from sounds by hearing. It occupies the upper part of the temporal lobe.

If one of the environmental sensors is a motion sensor, that is a device for recording limb and body positions and rotations, at least one brain sensor may be positioned at the motor cortex. The motor cortex is the part of the brain involved in planning, controlling and executing the movements of the body's muscles. It is located in the posterior part of the frontal lobe.

If one of the environmental sensors is a capacitive sensor, that is, a device for recording pressure, such as finger touch, at least one brain sensor may be positioned at the somatosensory cortex. The somatosensory cortex is the part of the brain that receives information from the surface of the body. It is located in the anterior part of the parietal lobe.

There is thus a connection between the type of environmental sensors and the location of the brain sensors. As will be seen later, the combination of the presence of the environmental sensors and the positioning of a brain sensor allows a synergistic effect of better-contextualized retrieved information.

Environmental sensors are sensors that aim to retrieve information about the environment of the device's user. This environment is defined by what surrounds this user. The elements that surround the user can manifest themselves to that person, and thus influence their mental behavior, in different ways: by sight, by sound (a feature produces noise, sound . . . ), etc.

As will be seen later, the role of these environmental sensors is to provide relevant information that can be matched with the brain data, and can thus, according to one embodiment, be used to contextualize that data. Generally speaking, data from environmental sensors are used to explain brain data which, alone, may be difficult to interpret.

According to one embodiment of the invention, at least one environmental sensor may be a video camera, oriented so as to capture an area of space substantially corresponding to that captured by the user's gaze. In other words, this camera is oriented towards the front of the device 1. The angle of view can be configured so as to capture a user's angle of view by taking into account typical eye movements.

Other cameras can be positioned and oriented differently in order to multiply the viewpoints of the user's environment.

According to one embodiment, a camera can be aimed at the user's face to capture their facial micromovements and/or their pupil movements.

Different video camera technologies may be used. They can be CCD (Charge Coupled Device), CMOS, infrared, etc. sensors, coupled with different optical devices (lenses, etc.). It is possible to consider a 360° camera for example.

According to one embodiment, at least one environmental sensor is a sound sensor. This sensor can typically be a MEMS sensor (standing for "Micro-Electro-Mechanical System"). The positioning of the sound sensors may vary depending on the nature of the sound to be acquired. Several sensors may be positioned so as to capture the sound environment as completely as possible. For example, two sensors may be positioned on either side of the device to capture the human environment like human ears.

Other possible environmental sensors include a gyroscope, a Real-Time Location System (RTLS), body sensors for acquiring data on body pulse, temperature, sweat, etc., weather data sensors, color data sensors, LIDARs, etc.

All these sensors provide a stream of environmental data that is transmitted to the processing means 15 of the device 1.

Furthermore, according to one embodiment of the invention, the device further comprises means for acquiring an external data stream from a source external to said device.

These means may include a radio interface and software and hardware means to communicate with this exterior source and perform appropriate signal processing.

This exterior source can be a video camera, for example a video surveillance camera. This video camera can provide additional information compared to the one(s) present in the device 1 by providing a global exterior view, probably larger but in any case different, from those acquired from the user's point of view via the device 1.

In the same way, this exterior source may be a sound sensor.

The source may be a weather data source, etc.

Some external data can be acquired by virtue of remote services, most often accessible in the form of APIs (Application Programming Interface) and requests over a network (for example the Internet).

The external data stream is transmitted to the processing means 15 of the device in the same way as the environmental data streams.

The device 1 therefore also comprises processing means.

These processing means make it possible to process the data streams and to exploit them.

More particularly, these means 15 are configured to
  select a signal extracted from the brain data stream,
  associate them with at least one corresponding signal extracted from the environmental (and external, in one embodiment) data stream,
  save these signals, and
  transmit them to a remote processing unit.

These processing means are typically implemented by one or more microprocessors, one or more memories and various specific components, as well as by software modules allowing the microprocessor(s) to perform the above-mentioned functions.

In particular, according to one embodiment, high-level processing functions such as selection and association can be implemented by a first means, or circuit, while storage is implemented by a storage means, or circuit, (essentially comprising a memory and circuits for managing this memory), and transmission can be provided by communication circuits.

The communication circuits can allow the connection to different types of access networks: cellular networks, especially $4^{th}$ or $5^{th}$ generation, local networks such as WLAN or WIFI, or proximity networks such as Bluetooth or NFC (Near Field Communication), etc.

The term "circuit" is understood in the present application as comprising hardware elements possibly associated with software elements insofar as certain hardware elements can be programmed. In particular, the term circuit comprises purely hardware implementations, in the form of specifically printed digital circuits or the like, implementations based, wholly or partially, on microprocessor or processor type features, which are subject to programming by software instructions stored in one or more associated memories, etc. The software instructions may consist solely of the instructions necessary for the basic operations of the processors (the "firmware") while the software instructions necessary for carrying out the functions of the embodiments of the invention may be stored either in these same memories associated with the processors, or in remote memories. In the latter case, these software instructions are present in the circuit only when the circuit is in operation to perform the functions according to the embodiments of the invention.

The device also has components necessary to operate autonomously. It may in particular have a power supply. That supply may comprise a rechargeable battery. The aforementioned means comprise antennas to ensure its connectivity, storage mechanisms (memories).

According to one embodiment of the invention, the device may comprise haptic feedback means (vibrating motor, osteophony, etc.) in order to improve the experience for the user and make them understand the processes initiated by the device.

Figure 2:
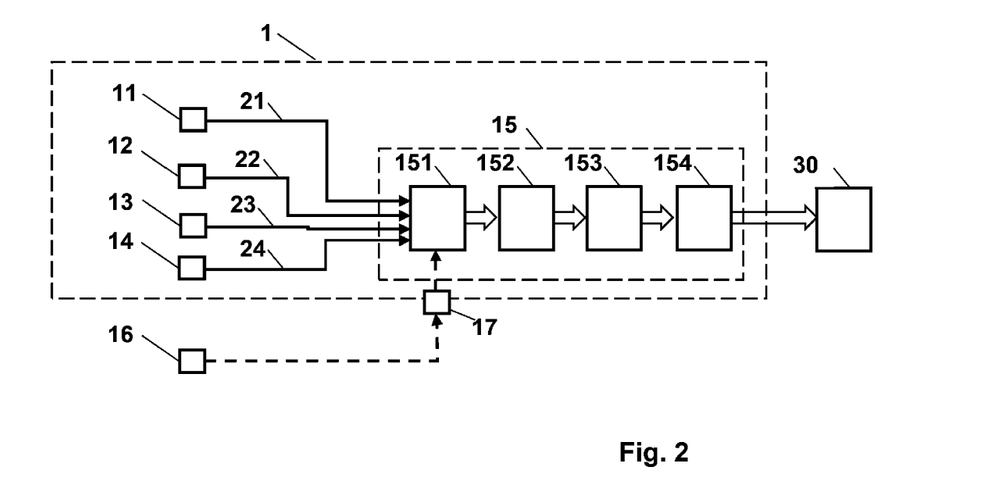
FIG. 2 shows an example functional arrangement of a device according to one embodiment of the invention.

FIG. 2 shows an example functional arrangement of a device according to one embodiment of the invention. This figure will be described in conjunction with FIG. 3 which shows a process according to one embodiment of the invention.

Two brainwave sensors 11, 12 are shown. In a step S1 in FIG. 3, they provide a data stream 11, 12 respectively, to the processing means 15.

This stream of brain data can be structured in many different ways, and the format of the data itself can also take many forms.

Figure 3:
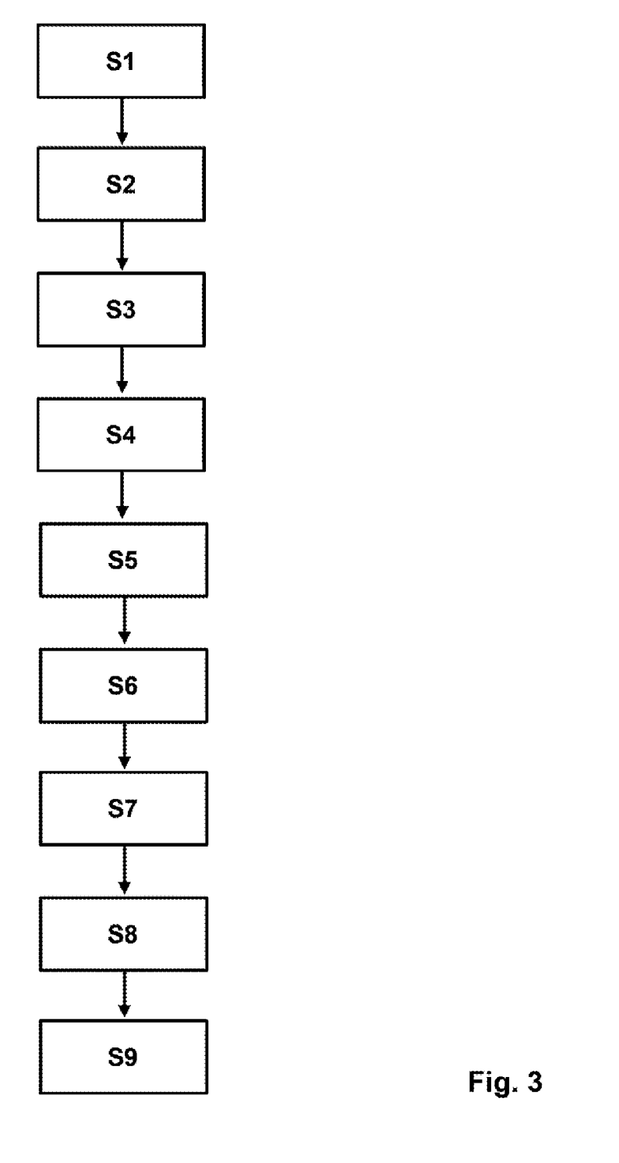
FIG. 3 shows, as a flowchart, a method according to one embodiment of the invention.

Two environmental sensors 13, 14 are shown. In a step S2, they provide a stream, respectively 23, 24, of environmental data to the processing means 15.

Also, according to one embodiment of the invention, an exterior source 16 can transmit an external data stream 26 to particular means 17 (radio interface, pre-processing means, etc.), configured to acquire and retransmit them to the processing means 15.

The processing means 15 can be subdivided into several functional modules 151, 152, 153, 154. As described earlier, these modules may be separate hardware components, or separate software modules, or a combination of both.

In a first step, the streams received from the different sensors are stored by storage means 151.

There is no mention here of a pre-processing module whose purpose would be to format the data received in a uniform and suitable format for further processing. This may include filtering, scaling, etc. These processes are conventional in themselves and directly accessible by the skilled artisan, familiar with the acquisition of raw data from various sensors for digital processing.

Then, in a step S3, the content of the memory is analyzed by an association module 152 in order to associate, or "match", the content of the brain data with the content of the environmental data (and external data if they exist).

This association is done by data packets. The storage means 151 are thus provided to allow at least one data packet (for each stream) to be stored in order to allow them to be associated in blocks by the association means.

More precisely, one may select a packet, or signal, in the brain data stream, and associate this signal with a "corresponding" signal in the different environmental (and external if they exist) data streams.

A signal (or packet) therefore contains data extracted from the streams. In the following, the terms "signal" and "data" may be used interchangeably, depending on the context, and the term "data" may imply "data contained in the signal".

A packet, or signal, may comprise the data contained in a time window, the size of which can be defined by the needs of the applications. This size can be determined by dynamic algorithms (for example recognition of an object in visual or auditory data: their recognition determines the end of the time window and thus "instantiates" the packet, or signal.

Also, depending on the application, the signals may contain only part of the data obtained from the sensors, or may contain pre-processed data (that is, data that has been pre-processed from the raw data, such as filtering, etc.)

Moreover, data acquisition can be done continuously at each iteration of the program set up by the processing means 15 and the sensors are sampled and synchronized.

According to one embodiment, a trigger event may be used to cause the device to not continuously read the data. The triggering event can be of different natures: detecting a face, a particular noise, a type of brainwave, etc. Once the trigger is targeted, the sensors are sampled and synchronized until the state no longer meets the targeting criteria.

According to one embodiment, for each signal of the brain data stream, the set of corresponding signals extracted from the environmental (and external if they exist) streams is associated. According to another embodiment, only a part of the signals extracted from the environmental (and external) streams can be associated.

As long as several brainwave sensors exist, the association can be made for each individual stream separately, or by grouping the streams from the different sensors into one global stream. In the latter case, the association can be made on this global stream.

However, these different implementations represent only implementation details and functionally amount to the same thing, since what matters is to associate brain data with environmental data, regardless of how these data are organized and then associated. It is indeed easy to convert one data structure into another, depending on the subsequent applications.

Once associated, the signals can be stored, in a step S4, by a storage module 153, within a local memory.

In particular, the brainwaves, expressed as acquired numerical values, are added to the values of the other sensors in a data structure that allows them to be grouped into packets.

Each type of data can be stored in different ways, particularly depending on its specificities.

For example, brain information can be stored by
Channels (that is by sensors),
Set of channels,
Time series,
Spectrograms, etc.
Visual data can be stored in the form of
images,
image sequences,
videos, etc.
Sound data can for example be stored in the form of
samples,
streams, etc.

These signals can also be associated with a timestamp and/or an identifier of the device 1

According to one embodiment, all these data can be stored in an array associating a signal extracted from a brain data stream, one or more signals extracted from environmental (and external if applicable) data streams and a timestamp.

By "array" we mean an association of a key with a value. An array can have different keys depending on the context to which values are associated.

An example of such an array is given below for illustrative purposes only.

| Brain signal | Environmental signal 1 | Environmental signal 2 | Timestamp | Identifier |
| --- | --- | --- | --- | --- |

This data may be hashed for data security purposes.

As an example, in an application where it is sought to associate brainwaves of a person with visual data of their environment when a coffee machine is present in it, the transmitted packet could be instantiated at the detection of the object in the user's environment by virtue of a camera and an object recognition algorithm.

In this example, this packet transmits a snapshot containing, at least:
the user's identifier,
the apparatus' identifier
the timestamp
the apparatus' configuration data
the raw data from the camera
the location and segmentation data of the object in the image
the brainwave recordings.

According to one embodiment, a latency time can be provided to temporally offset the brain signal with the corresponding environmental signals. Indeed, biological reality means that time is taken to transmit and process information. For example, an image arriving at the retina takes a few milliseconds before impacting the neurons. This time lag can be taken into account by the device.

A module 154 is configured to transmit them to a remote processing unit 30. This transmission corresponds to a step S5 in FIG. 3.

This transmission can be carried out in the course of time, upon the request of this remote device 30, in a periodic way, or according to any other possible embodiment allowing the communication of the associated data collected by the device 1.

This remote device 30 can thus acquire a large amount of data from the device 1. As has been seen, these data combine mental wave data with environmental data. The very nature of this "associated" data can allow a large number of applications and services to be implemented by this remote unit, in particular for the purpose of predicting an action to be carried out on the basis of at least one new signal extracted from a new brain data stream.

In general, this association allows a better understanding of the environmental context associated with mental data. It makes it possible to enhance the brain-machine interfaces by adding this contextual information and thus to improve the interpretation of mental data by a computer.

This association, which contextualizes brainwaves, can enable, for example, the real-time personalization of a classification model allowing a user to control an action on interactive objects in their environment.

For example, in the same way that some objects can be controlled via gestures detected by a camera, one embodiment of the invention can allow objects to be controlled via a thought instantiated by a brainwave signal.

Furthermore, this association makes it possible to build a database of contextualized brainwaves, that is associated with environmental data.

This database can be used to create a training set to create a predictive model.

Once a training set has been built, the predictive model can be trained. Once properly trained, such a predictive model can generalize the acquired information, and can predict unknown data on the basis of a model built on as large and diverse a training set as possible.

By virtue of the invention, the predictive model is trained on the basis of brain and environmental data, and in particular it can generalize a relationship between these two types of data.

The purposes of such a predictive model include the control of objects by thought, the monitoring of the mental states of an individual or a group of individuals, etc. Generally speaking, it makes it possible to determine an action to be performed from at least one new signal extracted from a new brain data stream.

It should also be noted that the training set is based on information from the perception of a real object and not, as in the previously mentioned article "*ThoughtViz: Visualizing Human Thoughts Using Generative Adversarial Network*", on images displayed on a screen and representing these objects.

However, it appears to the inventors that the difference between the perception of the representation of an object and the perception of the physical object itself induces a cognitive bias that creates a difference sufficient to invalidate the applicability of the experiment outside an experimental context.

Outside of an academic context and in the concrete case of mental control experiments, for example, training on real objects, and not on representations of these objects, allows a notable improvement in the system's performance.

Moreover, it favors a much stronger feeling of ownership for the user, and is also much less constraining to set up since it is enough to walk around and confront objects to, in an automatic and transparent way, allow the accumulation of cerebral and environmental data, while the device of the article requires the user remain seated in front of a screen for a much more tedious data acquisition. This results in a much larger, more quickly-generated data set (besides the fact that the data is enriched by the contribution of environmental sensors).

Thus, the device solves the first problem of taking into account a set of non-brain data contextualizing the acquired brain data and thus making it possible to give them meaning.

Thus, for an individual looking at a cat, we will be able to interpret the brain data as related to a cat or to this cat.

The device according to the invention also allows the creation of a training set, which is based on real data, sufficiently large and therefore easy and inexpensive to invest in.

According to one embodiment of the invention, associated data from different devices can be used.

This networking is possible within the framework of a single remote processing unit to which several devices are connected. It is also possible at the level of the devices themselves, which can either communicate with each other in "peer-to-peer" mode or have an interface allowing them to connect to a network in order to share their data.

In such a networking framework, it may be useful for the data to be associated with an identifier of the device that generated it.

Whatever the means of networking, it can be useful to obtain more global information about the mental activities of different users. In particular, it becomes possible to compare the mental activities of users confronted with similar environmental data. This aspect will be further detailed later, in connection with the extraction of classification information.

For example, networking allows the collection of brain data from people looking at the same object at the same time. This feature makes it possible to study the social reactions of the individuals in response to a visual, sound stimulus, etc.

It is also possible to pool data from different geographical locations by using long-distance communication networks (Internet, etc.). For example, we can collect brain data from people watching the same television program, in order to study their reactions in real time during the broadcast. It is thus possible to influence the course of this program according to an analysis of these reactions.

In a step S6, in FIG. 3, classification information is extracted from the collected (brain and environmental) data.

This step can be implemented by a remote processing unit. This remote device can be a personal equipment such as a computer, a tablet, a communication terminal such as a smartphone, etc., but it can also be a service provided by a server or a group of servers organized in a farm or abstracted as a cloud platform.

In another embodiment, this step is implemented by processing means of the device itself.

This classification information is information allowing forming sets of signals associated with step S3, which is extracted from the data itself, contained in the signals.

This classification information must be determined so that these sets are consistent and relevant, for example, for a given application.

In other words, the goal of this step is to classify the pairs of brain signals/environmental signals, in order to be able to constitute sets grouping the signals belonging to the same class. It therefore aims to both obtain a good quality of classification (each associated signal is in fact put in the right class) and have classes that are relevant to a given application, or more generally, that have a semantic meaning for a human being.

It is therefore necessary to analyze the data collected in order to determine the relevant classes for these groupings. Typically, these classes relate to a semantic concept that allows the contextualization of brain data.

It should be noted that this step S6 can be implemented at different times, and may not be mandatory in sequence with step S5, in the case where it is implemented directly by the device 1.

For example, the device (or devices, in the case of networking) may collect a large amount of data before the classification information extraction step S6 and subsequent steps are triggered. Alternatively, it can be triggered at the end of steps S4, S5, of memorization and transmission of signals or after the association step S3, etc.

Specifically, as examples, the extraction of classification information may involve:

At the time of acquisition of a data by a sensor (for example, a camera that looks for a given face or belonging to a given class);

At the time of data recording (for example, the audio signal is processed to recognize user utterances, and the raw audio is stored with any utterances recognized by the apparatus);

A posteriori, on the server, during a research phase not foreseen at the time of collection (for example, data have been recorded for several weeks, in a given location, and it is then sought to create coherent sets by grouping the brainwave samples by classes).

In one embodiment of the invention, this classification information directly provides labels to train a neural network (or other predictive model).

This classification information can also be used to perform searches. For example, it becomes easy to search by keyword ("meow", "green sweater", "construction noise", "blond person", "banana", etc.): these keywords are searched for among the classification information, and it is thus possible to retrieve all the associations between brain data and corresponding environmental data. This makes it possible to understand the activity of the human brain in a certain very specific context, indicated by the keywords, in particular by comparing the different brainwaves of a large number of people.

Such a study was not directly possible with state-of-the-art systems due to the impossibility of collecting brain data in large numbers and natively associated with environmental data allowing them to be contextualized.

In one embodiment, the classification information is determined from the environmental data (and/or external data).

For example, video data can be used to determine faces.

To do this, all or part of the environmental signals of the "video" type can be analyzed to determine the presence of a face therein. For each environmental signal wherein a face is determined, the associated brain signal can be recovered, as well as any other environmental and external signals. These different signals can then be associated with a corresponding classification information (by a keyword "face" or any other appropriate identifier).

The classification process can be more refined and determine different classes for male and female faces, for example, or smiling faces, etc.

The same process can be applied to other objects that can also be recognized in an image.

Different object recognition techniques (including facial recognition) can be used. In particular, various artificial intelligence techniques can be used, such as neural networks or support vector machines (SVMs).

Similarly, sound data can be used to identify specific sounds.

To do this, all or part of the environmental signals of the "audio" or "sound" type can be analyzed in order to determine the presence of an identifiable sound (engine noise, intelligible words, music . . . ) therein. For each environmental signal wherein such a sound is determined, the associated brain signal can be recovered, as well as any other environmental and external signals. These different signals can then be associated with a corresponding classification information (by a keyword "song" or any other appropriate identifier).

Here again, the analysis can be more refined, by defining different classes according to, for example, the recognition of the music (composer, performer, type of music, etc.), a semantic data determined from intelligible lyrics, etc.

In the latter case, an STT (Speech-To-Text) mechanism can be used to detect these words or sentences spoken by the user or by people around them.

Another example is the use of the user's position.

To do this, environmental signals from a position sensor are analyzed and classification information is determined from these locations. In particular, classes can be determined based on the distribution of acquired locations in the available data set. Thus, the geographical area corresponding to each class can be dynamically and automatically adapted to the available signals, so as to form non-zero and not too large cardinal classes.

For each environmental signal corresponding to the same classification information, the associated brain signal can be recovered, as well as any other environmental and external signals. These different signals can then be associated with a corresponding classification information (by a keyword identifying the place, a GPS coordinate, or any other appropriate identifier).

It is thus possible to create classes grouping the brain signals of the different people present in the same place. It is then easy to retrieve this information by a simple query with coordinates, which opens the door to a large number of new applications. A second extraction step can be considered to identify people who have looked at the same things in that location.

According to one embodiment, the classification information is determined from the brain data.

For example, it is possible to look for particular patterns in brain signals.

One possibility is to search for alpha patterns. Rhythmic electrical brain activities in humans are classified according to their frequency. The alpha rhythm is a brain rhythm, that is an electroencephalographic (EEG) oscillation resulting from the electrical activity of the brain, with a frequency of substantially 7.5 to 13 Hz. The alpha rhythm occurs when the person recorded as awake closes their eyes and relaxes.

In the same way as before, all the brain signals in which an alpha pattern has been detected are grouped in the same data set, together with the associated environmental and external data.

Classification information can be determined by a combination of environmental, brain and, if present, external data.

It is understood that depending on the environmental sensors present and the environmental signals they can generate, a wide variety of classification information can be extracted.

The choice of classification information may depend on the intended end-use applications and may be a configurable parameter via an appropriate interface.

It appears from the above examples that different technologies for extracting a class are possible. These include:

Machine learning: for example, such a mechanism can be used for the automatic recognition of an object in an image (via a convolutional neural network, for example), the identifier of this object constituting a classification information.

Classification by statistical or mathematical methods (for example, audio spectrum analysis, geolocation clustering, etc.)

In a step S7, a set associating these data, or signals, with the extracted classification information can be built. This set can be seen as a set of classes, with each class grouping the signal associations corresponding to the classification information corresponding to that class.

As mentioned, the extraction of classification information constitutes an automatic labeling of brain/environmental (and external) signal associations.

This set can be a training set for a machine-learning-based predictive model, such as a neural network.

According to one embodiment of the invention, a step of training S8 a neural network on the basis of this set created in step S7 can thus be provided.

Indeed, knowing for each pair of captured signals an extracted class, it is possible to automatically perform a supervised learning of a neural network by providing this pair as input and with a cost function depending on this extracted class.

According to one embodiment of the invention, therefore, an automatic labeling of the data captured by the various sensors is obtained. This characteristic is a very interesting advantage since the creation of a training set is a phase that can be very costly and time-consuming. In this case, it is a matter of collecting a large number of signals extracted from brain data streams and associating with them, usually manually, a label representative of what we want the model to predict.

According to one embodiment, in a step S9, at least one classification information can be predicted by providing at least one "new" signal extracted from the brain data as input to the neural network. This signal is "new" in the sense that it does not (usually) belong to the training set.

Once trained, the predictive model is able to generalize the new inputs to produce an output class probability. These classes, now generalizable to new entries, can be called "mental images".

Indeed, it is possible from brain signals, or a combination of brain signals and environmental (and external, if any) signals, to determine the corresponding mental image.

For example, at the mere thought of a cat, the method according to the invention is able to determine that the user of the device is thinking of a cat, with a certain probability.

Even more precisely, according to one embodiment of the invention, if users of the device are looking at cats, automatically and transparently to them, and if another user thinks of a cat, the method according to the invention will determine that he is thinking of a cat (even if he has never seen a cat while wearing the device).

It is then possible to determine an action to be taken from the predicted classification information. This action can be of different types, and depends on the considered application.

Depending on the considered applications, different types of neural networks can be considered. The choice of a type of neural network can influence some characteristics of the learning mechanism, during this step S8.

Examples include long-term memories, generative adversarial neural networks, convolutional neural networks, etc.

Long Short-Term Memory (LSTM) is an artificial recurrent neural network (RNN) architecture used in the field of deep learning. Unlike standard acyclic (or "feedforward") neural networks, LSTM has feedback connections. It can process not only single data points (such as images), but also entire sequences of data (such as speech or video).

This type of neural network is described in the following Wikipedia page: https://en.wikipedia.org/wiki/Long_short-term_memory, or in the thesis of Felix Gers, "*Long short-term memory in recurrent neural networks*", University of Lausanne, May 2001, DOI: 10.5075/epfl-thesis-2366

In learning, we provide the LSTM neural network with the extracted signals in the form of time series (that is typically a sequence of electrical values expressed in microvolts.)

Such a neural network can be used in different ways.

For example, a signal extracted from the brain data can be provided as input in the form of a time series. The network can then predict whether this signal belongs to the training set (this output is therefore Boolean).

An association between signals extracted from brain and contextual data can also be provided as input. In this case, the neural network can predict classification information.

Such a type of neural network can be used to enable a mental dematerialized signature of a user of the device 1 to be constituted. This mental signature can be used in the same way as an electronic or manual signature, in order to certify and secure an action of the user, in particular a transaction of monetary value: transfer of a security, banking transaction, etc.

In a learning phase, the user records his mental signature. It must be unique and difficult to imitate (especially to falsify) since it aims to validate his identity with third parties and to give his consent for certain transactions.

An application can guide the user by means of a human-machine interface in order to ask him to think about a succession of elements as distinct as possible (that is without any correlation detectable by a third party). For example, the user thinks, successively, of the image of his cat resting on a low wall in Corsica, of his lucky number, 3, of the lamb chop prepared on the barbecue every Wednesday by his grandmother, then, finally, of the smell of gasoline he loves so much.

While it records these 4 items, the application discerns in his brainwaves and in his behavior, the characteristics of each memory. The characteristics of each item will serve as constraints to create a model for an algorithmic classifier. The model thus created (and exported) constitutes the user's mental signature.

The thus exported signature can be saved, or stored, in a user's account. This storage can be local on the device or remote in order, particularly, to be used with other devices (but by the same user).

This signature, instantiated by the model constituted by the LSTM neural network, can be used to sign a new act, while making sure that the user is the one who recorded the signature initially.

To do this, the user must remember the sequence of these elements. The LSTM neural network can then provide a Boolean value indicating whether the brain signals resulting from this recollection match one of the examples of the training set, that is the previously recorded signature. The generalization capacity of the neural network makes it possible to allow some flexibility in the resemblance of the brainwaves.

The application can then refuse to continue the transaction if the mental signature does not match the one previously registered.

Another type of neural network that can be used is the Generative Adversarial Network (GAN). These algorithms were introduced by Ian J. Goodfellow, Jean Pouget-Abadie, Mehdi Mirza, Bing Xu, David Warde-Farley, Sherjil Ozair, Aaron Courville, and Yoshua Bengio, "Generative Adversarial Networks," in *Advances in Neural Information Processing Systems* 27, 2014. They make it possible to generate images with a high degree of realism.

In particular, a Constrained GAN (C-GAN) neural network can be used.

Such a network can be trained with signals extracted from video environmental data which are, in fact, successions of digital images.

Thus, in this embodiment, during the training phase, a series of images (from a video camera of the device 1) is provided together with a signal extracted from the brain data and possible other environmental data. This trained GAN can then be used to predict a new image from a new brain signal and possible associated environmental data. This image does not belong to the training set and is therefore a creation of the neural network from the provided data.

This technology can be exploited in different ways by applications using the automatic brainwave analysis device 1.

For example, one possible application is to put users' dreams into images.

To do this, the user must wear a device as previously described, in order to gather associations between brain data and environmental data (visual, sound, etc.), especially during the day. Over time, a vast library of associations is built up: people, landscapes, buildings, atmospheres, etc. are classified and each of these labeled elements is associated with the corresponding brain data (as previously described). A model can thus be generated for each element experienced by the user.

Once this learning phase has been completed, which can take several days, the user can then use the device to generate new environmental data (visual, sound, etc.) from the brain data.

This environmental data can be used to generate a medium via a human-machine interface, for example an image on a screen, a sound on a speaker, etc.

In particular, he can wear the device at night so that these new environmental data are generated based on his dreams. Thus, if the user is dreaming about a moment from a past day, the brainwave should have common features that allow the GAN to generate corresponding environmental data.

Prolonged use expands the reference "library" and improves the results because the probability of reliving an experienced situation in a dream increases. Similarly, the collection of dream memories grows day by day, giving the user a tangible way to remember what they experienced at night.

Another possible application of the same mechanism may concern a user who has fallen into a coma.

This user was previously using a device according to the invention.

After his hospitalization, he was made to wear the device in order to allow the generating, in real time, of environmental data associated with his thoughts. For example, the images associated with his thoughts and generated by the GAN neural network are displayed on a screen.

These images (or other environmental data) can be used by the user's family to try to understand the user's mental state. They can also allow to see, in real time, if their words and gestures have an impact on the generation of the images and thus to envisage a communication. Also, doctors can have a way to understand if the treatments administered are changing the mental states of the user in a coma.

Another example can allow a speaker to have real-time feedback on the mental states of his audience. At least some persons in his audience wear a device according to one embodiment of the invention. The measured brain data are provided to the GAN neural network which produces environmental data, for example images, as output.

These images are provided on a monitor for the speaker. They represent what the semantic content of his lecture evokes for the audience members.

This feedback can help the speaker to better understand the audience in order to adjust examples and stimulate the audience.

This image generation is made possible by previously collecting a large amount of brain data on many users of devices according to one embodiment of the invention. Thus, when audience members put on such a device for the first time, training is not necessary.

Another type of neural network is a convolutional neural network (CNN). This type of neural network is widely described in the literature and is subject to multiple variants. For example, you can refer to the corresponding Wikipedia page: https://fr.wikipedia.org/wiki/R%C3%A9seau_neuronal_convolutif, or to a generalist book such as "*Deep Learning*" by Ian Goodfellow, Yoshua Bengio, and Aaron Courville, MIT Press, 2016, ISBN 9780262035613.

Such a network can be used by providing as input, during a learning phase, a series of images of the representation of brain data in the form of spectrograms, for example. This spectrogram image can be generated by aggregating data from different brainwave sensors 11, 12, over a given time window (typically between 1 second and 10 seconds).

Once trained, the convolutional neural network can predict a class when presented with a new spectrogram, or a series of classes associated with a probability. For example, by providing as input a spectrogram of a user looking at, or thinking about, an animal, we can obtain as output class/probability associations of the type: Cat at 68%, dog at 27%, pigeon at 5% (all classes thus predicted forming a 100% partition).

An example of application of such a neural network can be the control of connected equipments, especially in a home automation context. The device, according to one embodiment of the invention, allows its user to control the home automation of his home by mere thought.

First, the user has to configure his system by training the CNN neural network.

To do this, a software application can be provided to guide this training phase. It can ask the user to imagine each command for each equipment he wants to control. Thus, the neural network can model the association between the brainwaves corresponding to the "imagining" of this command and the actual command of the equipment. This model can then be used for actual control using the neural network in prediction.

This mechanism can be very useful for added comfort, but also in a disability situation, since mere thought makes it possible to control a wide variety of equipment in the user's environment.

For example, a user has a motor disability. He needs to be as independent as possible at home to use his various appliances. His house is largely connected: television, household appliances, blinds, etc. Many of his appliances are connected to the local network of his house and are controllable by virtue of the MATTER standard that manufacturers of these various connected appliances take into account.

The user begins by putting on the device and initiating the control configuration to open and close the blinds in his home. To do this, he wants to imagine a blind closing and opening to control them. The application asks him to imagine several times the command to open the blinds. In turn, the user imagines a blind opening and does the same for the closing command. Once these first two commands are recorded, the application asks him to try them out to continue training and refining the mental image detection model of the blind opening and closing. The user takes action. He moves into the living room, looks at the blind, and imagines it closing. It is then that all the blinds in the house close. He does the same for the opening command. He can now configure all the controls one by one on all his appliances.

The command-recording process is time-consuming, but it saves time on a daily basis. Indeed, the user no longer needs to move or touch the button of a remote control to perform actions on his home automation. He can now permanently take control of his house. He can even activate the roaming option to keep control of his home automation even when he is away from home. Thus, before going home, he can turn on the heating with merely a thought.

Another example of application is the control of a prosthesis, a wheelchair, or an exoskeleton for a person with a motor disability.

In the example, a user is quadriplegic and uses a wheelchair. Controlling his chair is tiring. This is because the chair requires that he grasp a joystick and move it in the direction he wants to go.

To simplify the control of his chair, he got a device according to one embodiment of the invention. He will configure his chair to be controlled by the device's commands. To steer the chair, he will have to configure different mental images corresponding to different actions of his chair: turn left right, move forward, move backward, etc. Each action will correspond to a mental image that he will have to train so that the classification algorithm recognizes them.

To trigger the forward motion, he chooses to imagine his chair in motion from his point of view. As soon as the application asks him, he imagines his chair moving. He does the same for the other actions.

For fun, he decides to add a second control on the forward movement. Every time he thinks of a red Formula 1, he wants his chair to move forward too. He then adds an additional mental image, as requested by the application. The gamification of the controls allows him to set up his chair like a game and have a good time during configuration.

As soon as his chair is initialized with the mental images, he can move merely by imagining the movements of his chair. At any time, he can add new mental images to existing commands or delete all commands and start over.

Of course, the present invention is not limited to the examples and embodiment described and shown, but is defined by the claims. In particular, it is susceptible to numerous variants accessible to the skilled artisan.

The invention claimed is:

1. A system comprising one or more devices for automatic brainwave analysis, configured to be worn by a user, and a remote processing unit configured to store all of the signals from said one or more devices, said one or more devices having:
    at least one brainwave sensor, providing brain data stream associated with said user;
    at least one environmental sensor, providing an environmental data stream;
    one or more processors and one or more memories storing instructions configured to cause the one or more processors to:
        detect an object in an environment of said user based on said environmental data stream comprising visual and auditory data, and an object recognition algorithm;
        select a signal extracted from said brain data stream and contained in a time window determined based on a recognition of said object, for associating them with at least one corresponding signal extracted from said environmental data stream, for storing said signals and for transmitting them to said remote processing unit;
    said remote processing unit comprising one or more processors and one or more memories storing instructions for causing the one or more processors to:
        extract classification information from said data, and for constituting a set associating said data with the extracted classification information, said extracted classification being relevant for an application and constituting a label for said data, and
        train a neural network, based on said set, to predict a classification, from at least one new signal extracted from a new brain data stream and associated environmental data stream, and to determine an action of control to be carried out for said application,
    wherein said at least one environmental sensor comprises a video camera, oriented so as to capture an area of space substantially corresponding to that captured by the gaze of said user, and a sound sensor.

2. The system according to claim 1, further comprising a headband for holding said device in place on said user's head and for holding said brainwave sensors in contact with or in close proximity to said head; and a power supply for operating said sensors and said means.

3. The system according to claim 1, configured to associate with said signals a time stamp and/or an identifier of said device.

4. The system according to claim 1, wherein the location of the brainwave sensor depends on a type of said at least one environmental sensor.

5. The system according to claim 1, further comprising a communication interface acquiring an exterior data stream from a source exterior to said device,
    wherein the one or more processors and one or more memories of the one or more devices are further configured to execute:
    associating said signal extracted from said brain data stream with at least one corresponding signal extracted from said external data stream.

6. A method of automatically analyzing brainwaves using a device configured to be worn by a user, comprising:
    generating a brain data stream associated with said user by means of at least one brainwave sensor;
    generating an environmental data stream by means of at least one environmental sensor;
    detecting an object in an environment of said user based on said environmental data stream comprising visual and auditory data, and an object recognition algorithm;
    associating a selected signal extracted from said brain data stream and contained in a time window determined based on a recognition of said object, with at least one corresponding signal extracted from said environmental data stream;
    storing said signals and transmitting to a remote processing unit;

extracting, by said remote processing unit, of classification information from said data, and constituting a set associating said data with the extracted classification information, said extracted classification being relevant for an application and constituting a label for said data; and training, by said remote processing unit, a neural network based on said set to predict a classification, from at least one new signal extracted from a new brain data stream and associated environmental data stream, and to determine an action of control to be carried out for said application, wherein said at least one environmental sensor comprises a video camera, oriented so as to capture an area of space substantially corresponding to that captured by the gaze of said user, and a sound sensor.

7. The method according to claim 6, further comprising predicting classification information from at least one new signal extracted from the brain data.

8. A computer program having instructions for implementing the method according to claim 6 when executed on one or more information processing platforms.

\* \* \* \* \*

UNITED STATES PATENT AND TRADEMARK OFFICE
CERTIFICATE OF CORRECTION

PATENT NO. : 12,383,180 B2  
APPLICATION NO. : 18/046759  
DATED : August 12, 2025  
INVENTOR(S) : Bastien Didier Page 1 of 1

It is certified that error appears in the above-identified patent and that said Letters Patent is hereby corrected as shown below:

In the Claims

Column 17, Claim 1, Line 64, cancel the text beginning with "at least one brainwave" to and ending with "associated with said user;" in Line 65, and insert the following:
--at least one brainwave sensor, providing a brain data stream associated with said user;--

Signed and Sealed this  
Eighteenth Day of November, 2025

John A. Squires  
*Director of the United States Patent and Trademark Office*